United States Patent [19]

Nohda

[11] 4,067,646
[45] Jan. 10, 1978

[54] EYEGROUND INSPECTING CONTACT LENS

[75] Inventor: Masao Nohda, Kawasaki, Japan

[73] Assignee: Nippon Kogaku K.K., Tokyo, Japan

[21] Appl. No.: 666,318

[22] Filed: Mar. 12, 1976

[30] Foreign Application Priority Data

Mar. 17, 1975  Japan .............................. 50-35824[U]

[51] Int. Cl.$^2$ .............................................. A61B 3/10
[52] U.S. Cl. .......................................... 351/6; 351/16
[58] Field of Search .................................. 351/6, 7, 16

[56] References Cited

U.S. PATENT DOCUMENTS

3,820,879  6/1974  Frisen ................................. 351/6 X

FOREIGN PATENT DOCUMENTS

466,329  10/1951  Italy ........................................ 351/6

OTHER PUBLICATIONS

"Allen Moncoscope Prism," *Bausch & Lomb*, Sept. 1947.

*Primary Examiner*—Paul A. Sacher
*Attorney, Agent, or Firm*—Fitzpatrick, Cella, Harper & Scinto

[57] ABSTRACT

An eyeground inspecting contact lens adapted to be disposed in contact with the cornea of an eye to be inspected, in order that an illuminating light may be directed to the fundus of the eye so as effectively to illuminate the same for the observation of the eyeground, comprises a plurality of glass bodies having the incidence surface thereof inclined with respect to the optical axis. The refractive indices of the glass bodies, the inclined angle of the incidence surface with respect to the optical axis and the inclined angle of the boundary surface of each of the glass bodies with respect to the optical axis are selected such that, of the illuminating light flux, the light beam coincident with the optical axis prior to incidence on the first glass body is made parallel to but spaced from the optical axis after being passed through the glass bodies, and then impinges on the eyeground.

9 Claims, 7 Drawing Figures

EYEGROUND INSPECTING CONTACT LENS

BACKGROUND OF THE INVENTION

1. Field of the Invention

This invention relates to a contact lens which is used for observing the fundus or eyeground with the aid of a slit lamp or the like.

2. Description of the Prior Art

When the eyeground is to be observed with the aid of a slit lamp, an auxiliary lens such as an eyeground inspecting contact lens, or a ruby lens having a great negative refractive power, or an auxiliary lens like a bayadi lens having a great positive refractive power is used to correct the refractive power of the eye.

Observation of the eyeground always involves the necessity of illuminating the eyeground to be observed and, therefore, part of the illuminating light flux is reflected by the auxiliary lens or by the surface of the cornea and this greatly interferes with the observation. For this reason, the most popular known eyeground inspecting contact lenses have been those having a single boundary surface with respect to the air, that is, having only one surface that produces the harmful reflected light. However, these known lenses have been characterized by the cumbersomeness with which such contact lenses are mounted to the corneas of the eyes to be inspected.

A typical eyeground inspecting contact lens according to the prior art is shown in FIG. 1 of the accompanying drawings wherein numberal 1 designates the eye to be inspected, and 2 denotes the eyeground inspecting contact lens formed in a conical shape which has one end face adapted for intimate contact with the cornea surface of the eye to be inspected, and the other end face 2' serving as the incidence surface for the illuminating light flux. Designated by 3 is a light source (or an optical system) for illuminating the eyeground, and 4 an inspector's eye (or an eyeground observing optical system). Numberal 5 indicates a condenser lens and 6 a half-mirror by which the light flux passed from the light source 3 through the condenser lens 5, is directed toward the contact lens 2. X-X' is the observation axis on which the inspector's eye 4 may observe the fundus of the eye 1 to be inspected.

Inspection of the fundus or eyeground is carried out with the inspecting contact lens 2 mounted on the eye 1 to be examined, as shown in FIG. 1, and the observation of the eyeground requires the eyeground to be illuminated by the light source 3 as already described. However, part of the illuminating light flux is reflected by the incidence surface 2' of the inspecting contact lens 2 and enters the inspector's eye 4 to interfere with his observation (as indicated by R in FIG. 1).

In recent surgical operations photo-concentration techniques have been utilized in which a flux of intense light from a xenon lamp or a laser is focused on the eyeground to burn the same, but in this case, if the harmful reflected light as described above should occur at all, it would not only cause interference with the observation, but would also be very dangerous to the inspector's eye.

SUMMARY OF THE INVENTION

Accordingly, I have conceived the present invention to provide an eyeground inspecting contact lens which avoids the foregoing difficulties and disadvantages. As a feature of my invention, I contribute an inspection contact lens of the class described which utilizes a combination of a plurality of prisms with different refractive indices and which entirely eliminates the harmful reflected light which has been caused by the incidence surface of the above-described eyeground inspecting contact lens according to the prior art.

According to another feature of the present invention, the eyeground inspecting contact lens comprises a plurality of glass bodies having the incidence surface thereof inclined with respect to the optical axis. The refractive indices of the glass bodies, the inclined angle of the incidence surface with respect to the optical axis, and the inclined angle of the boundary surface of each of the glass bodies with respect to the optical axis are selected such that, of the iluminating light flux, the light beam coincident with the optical axis is made parallel to the optical axis after passing through the glass bodies, and then impinges on the eyeground.

There has thus been outlined rather broadly the more important features of the invention in order that the detailed description thereof that follows may be better understood, and in order that the present contribution to the art may be better appreciated. There are, of course, additional features of the invention that will be described hereinafter and which will form the subject of the claims appended hereto. Those skilled in the art will appreciate that the conception upon which this disclosure is based may readily be utilized as a basis for the designing of other structures for carrying out the several purposes of the invention. It is important, therefore, that the claims be regarded as including such equivalent constructions as do not depart from the spirit and scope of the invention.

BRIEF DESCRIPTION OF THE DRAWINGS

Specific embodiments of the invention have been chosen for purposes of illustration and description, and are shown in the accompanying drawings forming a part of the specification wherein.

DESCRIPTION OF THE PREFERRED EMBODIMENTS

Figure 1:
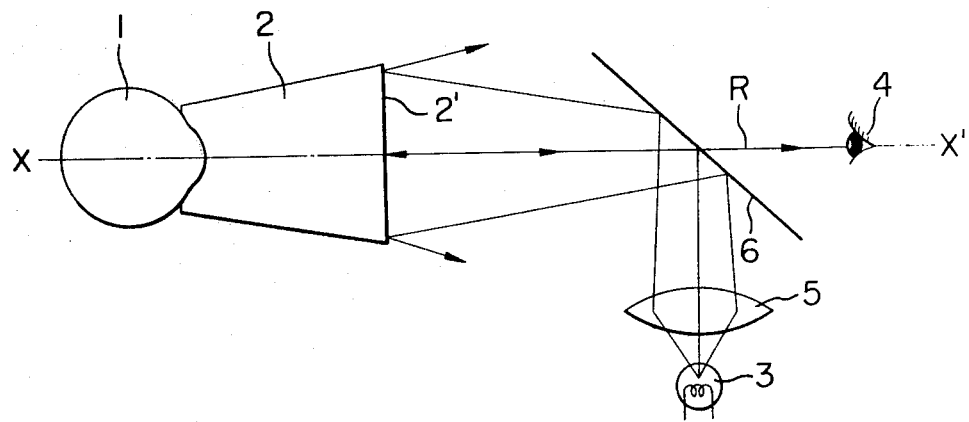
FIG. 1 schematically illustrates an eyeground inspecting contact lens according to the prior art.
Figure 2:
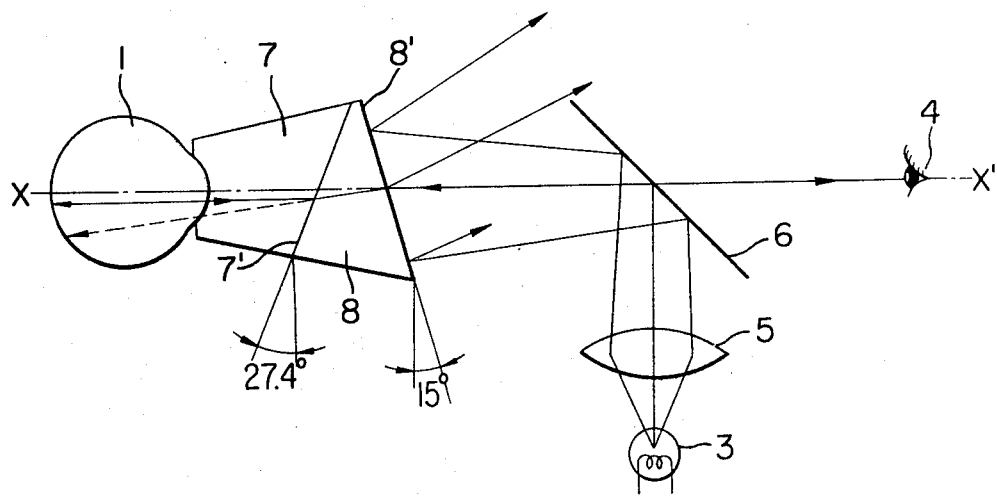
FIG. 2 is a schematic illustration of a first embodiment of the present invention.

Referring to FIG. 2, a first embodiment of the present invention includes glass bodies 7 and 8 different in refractive index and having prism-like cross sections, as shown. Designated by 7' is the joint surface (boundary surface) of the glass bodies 7 and 8, and 8' is the incidence surface of the glass body 8.

Figure 6:
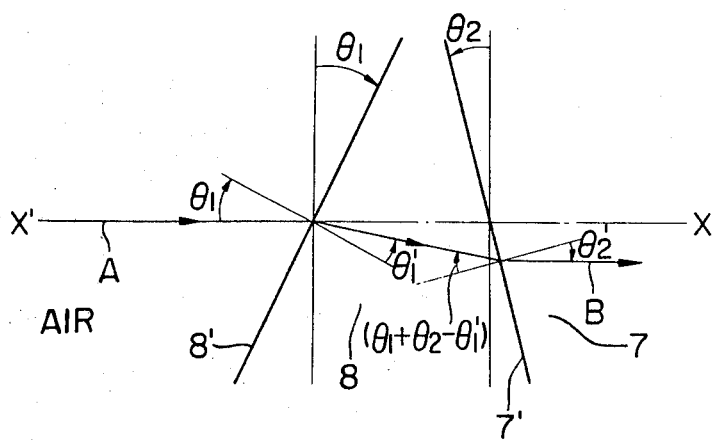
FIG. 6 is a diagrammatic representation of the first embodiment shown in FIG. 2.

The refractive indices $n_1$ and $n_2$ of the glass bodies 8 and 7, respectively, the inclined angle $\theta_1$ of the incidence surface 8' with respect to an observation optical axis X-X', and the inclined angle $\theta_2$ of the boundary surface 7' with respect to the optical axis are selected such that, of the illuminating light rays entering the incidence surface 8', the lens-entering light beam coincident with the optical axis X-X' is again made parallel to the optical axis X-X' after being refracted twice by the glass bodies 7 and 8, and then impinges on the eyeground. This will more particularly be described by reference to FIG. 6 which diagrammatically shows the first embodiment of FIG. 2. In FIG. 6, the angles are given positive and negative signs in accordance with their clockwise and counterclockwise inclinations with respect to the vertical to the optical axis.

In FIG. 6, the incident light ray A is reflected at the boundary surface 7' with the following relations established:

$$\sin\theta_2' = (n_1/n_2) \sin(\theta_1 + \theta_2 - \theta_1') \qquad (1)$$

The condition for the incident light ray A and the emergent light ray B to be parallel to each other is that $\theta_2' = -\theta_2$. Thus, under the condition that $\theta_2' = -\theta_2$, the aforementioned refractive indices $n_1$ and $n_2$ and the inclined angles $\theta_1$ and $\theta_2$ may be selected within respective ranges which will satisfy the equation (1). In the first embodiment shown In FIG. 2, the refractive index of the glass body 8 is $n_1 = 1.53172$, that of the glass body 7 is $n_2 = 1.79668$, the inclined angle of the incidence surface 8' is $\theta_1 = 15°$ and that of the boundary surface 7' is $\theta_2 = 27°24'$.

In the above-described construction of the present embodiment, with the eyeground inspecting contact lens 7, 8 mounted on the eye 1 to be inspected, and referring to FIGS. 2 and 6, the illuminating light flux from the light source 3 is first passed through a lens 5 and a half-mirror 6, and then split into a transmitting light beam and a reflected light beam by the incidence surface 8'. The transmitting light beam illuminates the eyeground to be observed, while the reflected light beam is reflected not toward the inspector's eye 4, but upwardly as shown, because the incidence surface 8' of the glass body 8 is inclined with respect to the observation optical axis X-X'. Thus, the reflected light beam does not interfere with the observation.

On the other hand, the illuminating light flux entering the incidence surface 8'is refracted twice when it passes through the glass bodies 8 and 7, and of such illuminating light flux, the light beam having entered in parallelism to the optical axis X-X' is made parallel to, but slightly spaced from, the optical axis X-X' after said two refractions and then impinges on the fundus of the eye to be inspected, from which such illuminating light beam is reflected to travel back along the same path and through the half-mirror 6 to the inspector's eye 4.

Therefore, when the eyeground is observed through the eyeground inspecting contact lens 7, 8, no prism action occurs in spite of the inclination of the incidence surface 8' of the glass body 8, thereby enabling the observation of the eyeground at a point thereof somewhat parallel-displaced from the observation angle X-X'. The small degree of parallel displacement of the observation axis will form no practical inconvenience to the eyeground observation.

Figure 3:
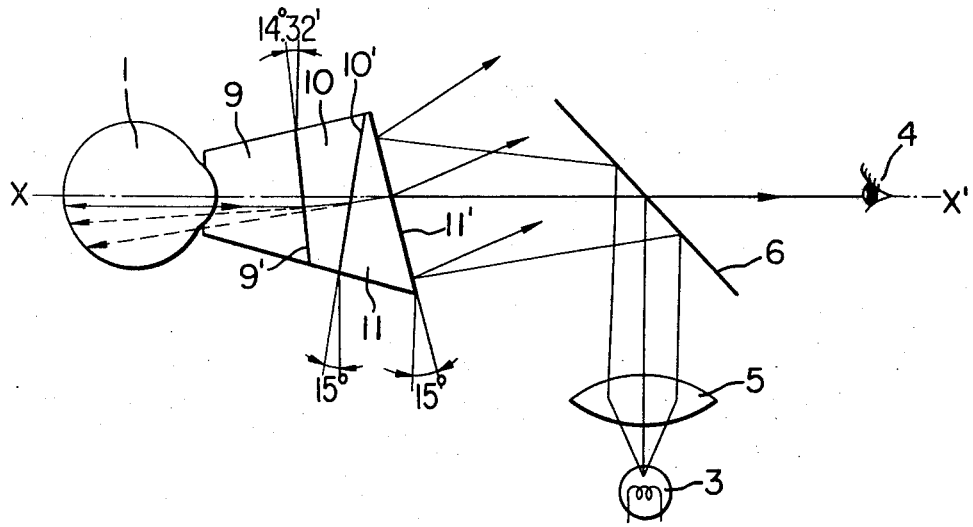
FIG. 3 is a schematic illustration of a second embodiment of the present invention.
Figure 7:
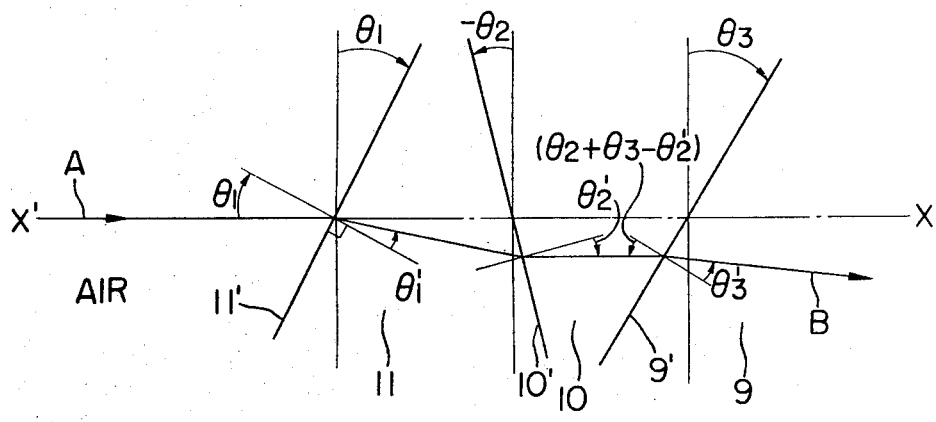
FIG. 7 is a diagrammatic representation of the embodiments shown in FIGS. 3 to 5.

As a method of bringing the above-described eyeground observation point closer to the observation optical axis X-X', it will come to mind to provide another glass body in addition to the glass bodies 7 and 8 of the first embodiment. FIG. 3 shows a second embodiment of the present invention. In FIG. 3, glass bodies 9, 10 and 11 differ in refractive index and have prism-like cross sections, as shown. Designated by 9' is the joint surface (boundary surface) of the glass bodies 9 and 10, and 10' the joint surface (boundary surface) of the glass bodies 10 and 11, and 11' the incidence surface of the glass body 11. The refractive indices $n_1$, $n_2$ and $n_3$ of the glass bodies 9, 10 and 11, the inclined angle $\theta_1$ of the incidence surface 11' with respect to the observation optical axis X-X', the inclined angle $\theta_2$ of the boundary surface 10' with respect to the optical axis X-X', and the inclined angle $\theta_3$ of the boundary surface 9' with respect to the optical axis are selected such that, of the illuminating light flux entering the incidence surface 11', the illuminating light beam coincident with the optical axis X-X' is made parallel to, but slightly spaced from, the optical axis X-X' after being thrice refracted by the glass bodies 9, 10 and 11, and then impinges on the eyeground. This will more particularly be described by reference to FIG. 7 which diagrammatically illustrates the second embodiment. In FIG. 7, the angles are given positive and negative signs in accordance with their clockwise and counterclockwise inclinations with respect to the vertical to the optical axis.

In FIG. 7, the incident light ray A is refracted at the boundary surface 9' with the following relation established:

$$\sin\theta_3' = (n_2 n_3)\sin(\theta_2 + \theta_3 - \theta_2') \qquad (2)$$

The condition for the incident light ray A and the emergent light ray B to be parallel is that $\theta_3' = \theta_3$. Thus, under the condition that $\theta_3' = \theta_3$, the refractive indices $n_1$, $n_2$ and $n_3$ and the inclined angles $\theta_1$, $\theta_2$ and $\theta_3$ may be selected within respective ranges which will satisfy the equation (2).

In the second embodiment shown in FIG. 3, the refractive index of the glass body 11 is $n_1 = 1.53172$, that of the glass body 10 is $n_2 = 1.79668$, that of the glass body 9 is $n_3 = 1.53172$, the inclined angle of the incidence surface 11' is $\theta_1 = 15°$, that of the boundary surface 10' is $\theta_2 = 15°$, and that of the boundary surface 9' is $\theta_3 = 14°32'$.

According to this embodiment, with the eyeground inspecting contact lens 9, 10 and 11 mounted on the eye 1 to be inspected, the illuminating light flux from the light source 3 is passed through the lens 5 and the half-mirror 6, and is then split into a transmitting light beam and a reflected light beam by the incidence surface 11' of the glass body 11. The transmitting light beam illuminates the eyeground to be observed, while the reflected light beam is reflected not toward the inspector's eye 4, but upwardly as shown, because the incidence surface 11' is inclined with respect to the observation optical axis X-X'. Thus, the reflected light beam does not interfere with the observation.

On the other hand, the illuminating light flux entering the incidence surface 11' is refracted thrice when it passes through the glass bodies 11, 10 and 9, and of such illuminating light flux, the light beam having entered in parallelism to the optical axix X-X' is made parallel to the optical axis X-X' after the said three refractions, and then impinges on the fundus of the eye to be inspected, from which such illuminating light beam is reflected to travel back along the same path and through the half-mirror 6 to the inspector's eye 4.

Figure 4:
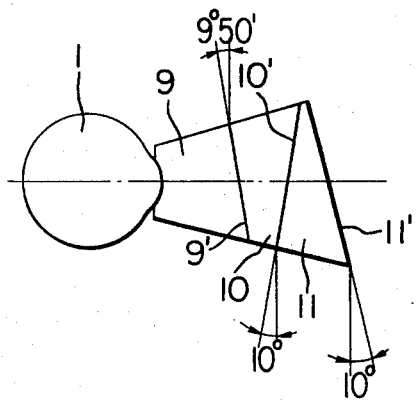
FIG. 4 is a schematic illustration of a third embodiment of the present invention.

FIG. 4 shows a third embodiment of the eyeground inspecting contact lens in which the refractive index of the glass body 11 is $n_1 = 1.53172$, that of the glass body 10 is $n_2 = 1.79668$, that of the glass body 9 is $n_3 = 1.53172$, the inclined angle of the incidence surface 11' is $\theta_1 = 10°$, that of the boundary surface 10' is $\theta_2=10°$ and that of the boundary surface 9' is $\theta_3=9°50'$.

Figure 5:
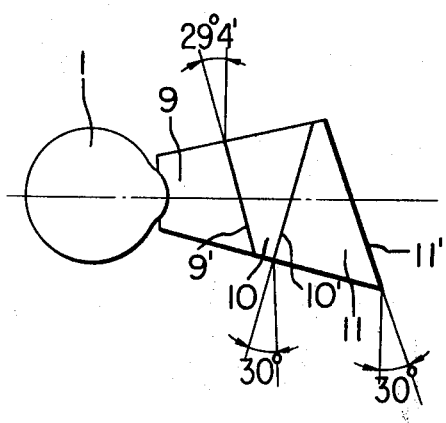
FIG. 5 is a schematic illustration of a fourth embodiment of the present invention.

FIG. 5 shows a fourth embodiment of the eyeground inspecting contact lens in which $n_1=1.53172$, $n_2=1.79668$, $n_3=1.53172$, $\theta_1=30°$, $\theta_2=30°$ and $\theta_3=29°4'$.

I believe that the construction and operation of my novel eyeground inspecting contact lens will now be understood and that the advantages thereof will be fully appreciated by those persons skilled in the art.

I claim:

1. An eyeground inspecting contact lens adapted to be disposed in contact with the cornea of an eye to be inspected, in order that an illuminating light may be directed to the fundus of the eye so as effectively to illuminate the same for the observation of the eyeground, said contact lens comprising a plurality of glass bodies having the incidence surface thereof inclined with respect to the optical axis, the refractive indices of said glass bodies, the inclined angle of said incidence with respect to the optical axis and the inclined angle of the boundary surface of each of said glass bodies with respect to the optical axis being selected such that, of the illuminating light flux, the light beam coincident with the optical axis prior to incidence on the first glass body is made parallel to but spaced from the optical axis after passing through said glass bodies, and then impinges on the eyeground.

2. An eyeground inspecting contact lens according to claim 1, wherein said contact lens comprises two glass bodies.

3. An eyeground inspecting contact lens according to claim 2, wherein the inclined angle $\theta_1$ of the incidence surface of said lens with respect to the observation optical axis, the inclined angle $\theta_2$ of the boundary surface of said two glass bodies with respect to the optical axis and the refractive indices of the glass bodies satisfy the formula:

$$\sin\theta_{2'} = (n_1/n_2) \sin(\theta_1 + \theta_2 - \theta_1')$$

where $n_1$ is the refractive index of the glass body remote from the eye to be inspected;

$n_2$ is the refractive index of the glass body adjacent the eye to be examined; and $\theta_1'$ is the angle between a plane perpendicular to the lens incidence surface and the path of said light beam between said incidence and said boundary surfaces.

4. An eyeground inspection contact lens according to claim 3, wherein $n_1=1.53172$, $n_2=1.79688$, $\theta_1=15°$ and $\theta_2=27°24'$.

5. An eyeground inspection contact lens according to claim 1, wherein said lens comprises three glass bodies.

6. An eyeground inspection contact lens according to claim 5, wherein the respective refractive indices $n_2$ and $n_3$ of the central glass body and that remote from the eye to be examined, and the respective inclined angles, $\theta_2$ of the boundary surface between the third glass body remote from the eye to be examined and the central glass body, and $\theta_3$ of the boundary between the central glass body and the first glass body adjacent the eye to be examined satisfy the formula:

$$\sin\theta_3' = (n_2/n_3) \sin(\theta_2 + \theta_3 - \theta_2')$$

where $\theta_3'$ is the angle between a plane perpendicular to the boundary surface between the central glass body and the glass body adjacent the eye to be examined and the path of the light beam passing through the latter glass body; and $\theta_2'$ is the angle between a plane perpendicular to the boundary between the glass body remote from the eye to be examined and the central glass body and the path of the light beam through the central glass body.

7. An eyeground inspection contact lens according to claim 6, wherein the refractive index of said first glass body is 1.53172, of the central glass body is 1.79668, and of the third glass body is 1.53172, the inclined angle of the incidence surface is 15°, of the boundary surface between the first and central bodies is 15°, and of the boundary surface between the central and third bodies is 14°32'.

8. An eyeground inspection contact lens according to claim 6, wherein the refractive index of said first glass body is 1.53172, of the central glass body is 1.79668 and of the third glass body is 1.53172, the inclined angle of the incidence surface is 10°, of the boundary surface between the first and central bodies is 10° and of the boundary surface between the central and third bodies is 9°50'.

9. An eyeground inspection contact lens according to claim 6, wherein the refractive index of said first, central and third glass bodies are, respectively, 1.53172, 1.79668, and 1.53172, the inclined angle of the incidence surface is 30°, of the boundary surface between the first and central bodies is 30°, and of the boundary surface between the central and third bodies is 20°4'.

* * * * *

UNITED STATES PATENT AND TRADEMARK OFFICE
CERTIFICATE OF CORRECTION

PATENT NO. : 4,067,646
DATED : January 10, 1978
INVENTOR(S) : MASAO NOHDA

It is certified that error appears in the above-identified patent and that said Letters Patent are hereby corrected as shown below:

Column 4, line 25, change "$n_2 n_3$" to -- $\frac{n_2}{n_3}$ --.

Column 5, line 20, after "incidence" insert --surface--.

Signed and Sealed this

Eighteenth Day of April 1978

[SEAL]

Attest:

RUTH C. MASON
Attesting Officer

LUTRELLE F. PARKER
Acting Commissioner of Patents and Trademarks